US00PP09256P

United States Patent [19]

Felker et al.

[11] Patent Number: Plant 9,256

[45] Date of Patent: Aug. 22, 1995

[54] TEXAS NATIVE THORNLESS MESQUITE 'BETH'

[76] Inventors: Peter Felker, 278 B, Co. Rd. 1036, Kingsville, Tex. 78160; Andrew Korus, Rte. 1 Box 148, Stockdale, Tex. 78160

[21] Appl. No.: 126,875

[22] Filed: Sep. 27, 1993

[51] Int. Cl.[6] ..... A01H 5/00

[52] U.S. Cl. ..... Plt./51.1

[58] Field of Search ..... Plt. 51.1

[56] References Cited

PUBLICATIONS

Klass, S. et al., (1985) "Optimizing the environment for rooting cuttings of highly productive clones of *Prosopis alba*" (mesquite/algarrobo) *Journal of Horticultural Science* vol. 60, 275–284.

Wojtusik, T. et al, (1993) "Interspecific graft incompatibility in *Prosopis*" Forest Ecology and Management, vol. 59 pp. 329–340.

Burkart, A., (1976) "A Monograph of the Genus *Prosopis*", *Journal of the Arnold Arboretum*, pp. 219–221, 495, 496, 514, 515, 497, 519–522.

Johnston, M. C., "The North American Mesquites *Prosopis Sect. Algarobia* (Leguminosae)" *Brittania* vol. 14 (1962) pp. 72–90.

*Primary Examiner*—James R. Feyrer

[57] ABSTRACT

A new and distinct Native Mesquite Tree, *Prosopis glandulosa* which is particularly characterized by its complete thornlessness, its tolerance of cold to −15 C., its extreme upright habit, its formation of a tree of good symmetry and balance, and by its adaptation to dry desert areas in the United States. The tree of this discovery presents an attractive shade tree to the landscape industry which does not require undue amounts of irrigation, and which will mature into a tall attractive specimen at full maturity.

5 Drawing Sheets

BACKGROUND OF THE INVENTION

The tree is a new and distinct native Texas Thornless Mesquite Tree, *Prosopis glandulosa.* The species of this tree is of interest to those living in the dry sun belt areas of the United States because of its ability to live on scant quantities of water, live in elevated temperatures, yet survive extended temperatures as low −15 C. Accordingly, the potential value of this tree as a shade tree in desert environments is noteworthy. The foliage of this tree might constitute feed for livestock under conditions of extreme drought, and the value of wood chips from Mesquite for smoking foods, like meats, is notorious. The potential food value of pods harvested from this species is also known, and shown by the historical use of them by native Americans and early settlers as candy. The tree of this invention enjoys each of these noted advantages and forms an upright tree of unusual habit for the species *P. glandulosa.*

The tree of this invention has discovered on land which had been converted from crop production to a managed pasture under cultivation. The original specimen was retained along with other trees, to provide shade and protection for livestock to be grazed on the land. As the trees matured, it was noticed that this tree was very unusual in form and appearance for trees *P. glandulosa.* It became apparent that this tree had a form and appearance unusual for native mesquite trees; as well as being thornless. Being an unusually and conspicuously attractive tree with desert adaptation, the value of the tree for potential use in landscape appointments became manifest. Following the discovery and observation of the tree, steps were taken to reproduce the tree so that it could be further observed and tested toward possible introduction of the tree to commerce as a shade tree which would tolerate desert conditions of, for example the Southwestern United States. The tree of this invention was initially asexually reproduced by air layering of specimens from the first tree discovered on the farm of the discoverer, Mr. Andrew Korus, near Stockdale, Tex., and later by rooted cuttings at the facilities of Plantclone, Inc. in Kingsville, Tex. After observation of such clonal reproductions, it has been determined that all clones of the tree are identical to the originally discovered tree in all distinguishing characteristics.

SUMMARY OF THE INVENTION

The tree of this invention is unusual for the species and differs from other trees of the same botanical species in the following combination of characteristics:

The tree is virtually thornless. This is of clear advantage to the homeowner.

The tree of this invention is cold tolerant to temperature of −15 C., which is much colder than is tolerated by thornless Argentine *Prosopis alba* species which are the only other thornless *Prosopis* used for ornamental purposes.

The tree will actively grow in unusually dry summers, to attain a height of about 10 m tall in about 30 years.

The tree is essentially upright, rather than being broad and weeping as usually characterizes trees of this species. The tree has one trunk leading to plural nondominant, nearly vertical primary branches which arise in close spacing and narrow angles from points at about chest height.

The tree is moderate to light canopy density and stately in pose.

The foliage of this tree is characterized as having virtually one pair of pinnae per leaf, and having pinnae of about 10 pair, or more leaves per pinnas, rendering a tree which is at least as water efficient as any of the species that we have observed.

The tree of this discovery is capable of asexual reproduction by rooting cuttings and by grafting. However, well rooted cuttings are very susceptible to root rots. Thus grafting onto native rootstock is the primary commercial technique for commercial asexual propagation. The above combination of characteristics set this tree apart from others of the species and characterize a tree which constitutes a valuable extreme within the range of expression of the species which is particularly adapted for culture as a shade tree which will flourish in the dry, hot desert areas of this country with minimal irrigation or no irrigation at all.

DESCRIPTION OF THE VARIETY

Figure 1:
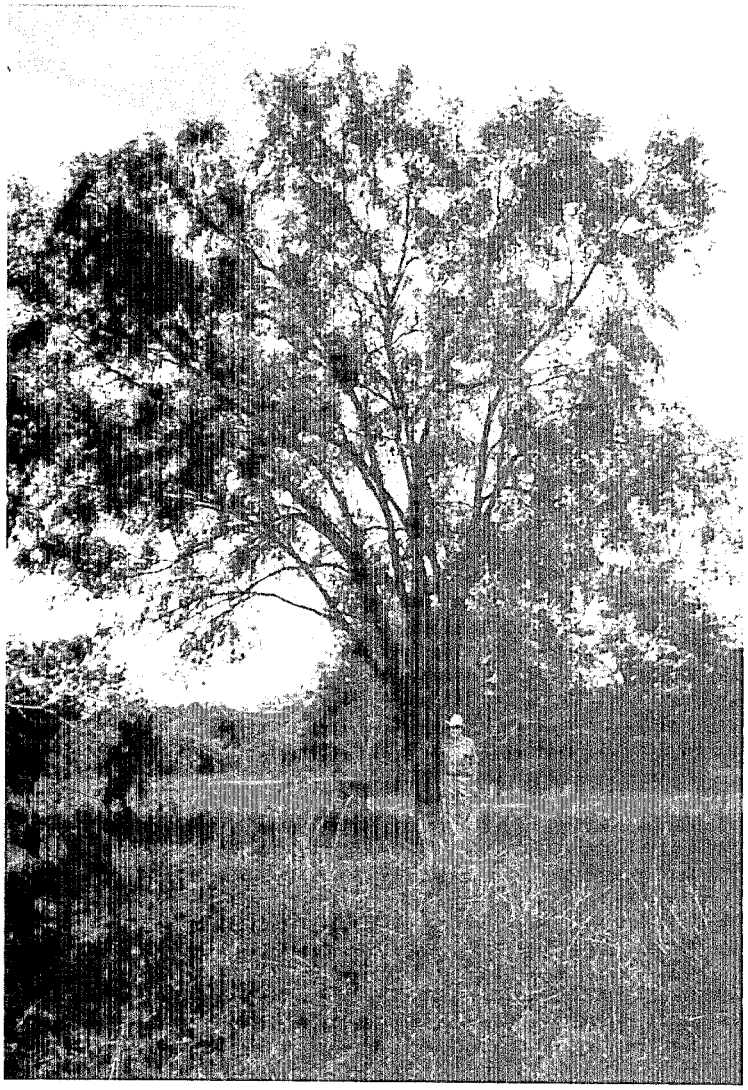
FIGS. 1 and 5 show the original specimen of the tree, and show the unusual upright growth habit of the tree with the single trunk, plural, upright primary branches, and the density of the secondary branches and foliage of this discovery.
Figure 2:
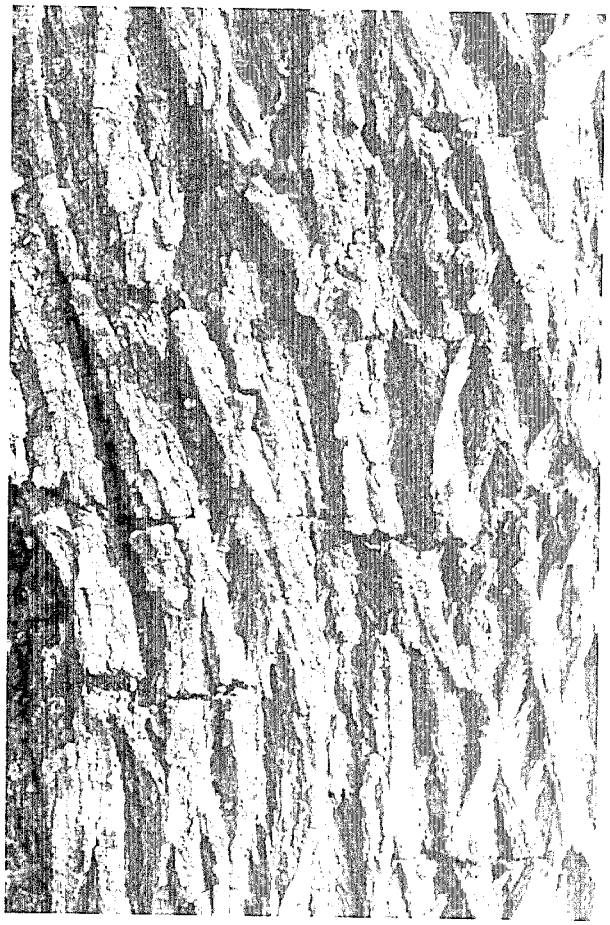
FIG. 2 is a color photograph of the bark of the mature tree.
Figure 3:
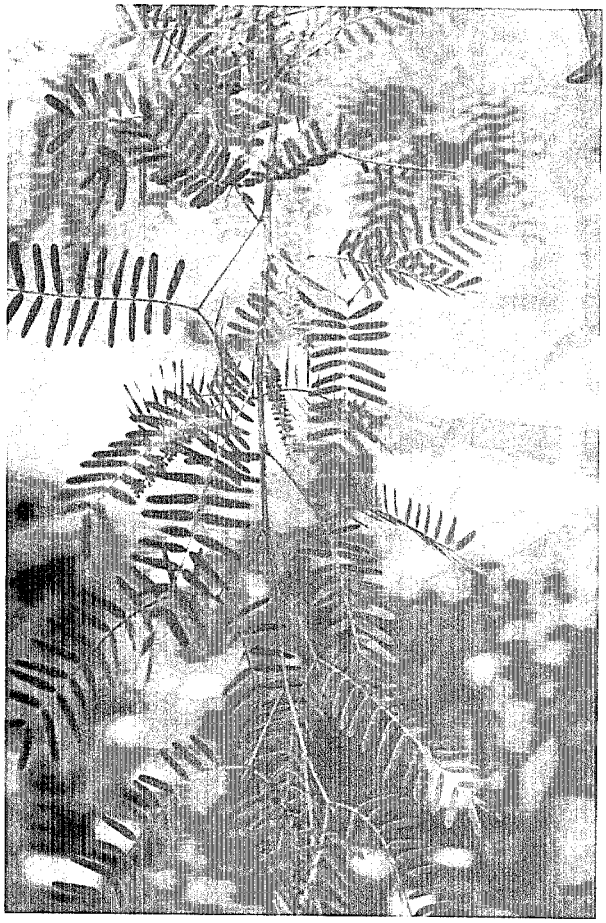
FIG. 3 is a color photograph of a young stem of the asexually propagated tree, with foliage and flowers, showing complete lack of spines.
Figure 4:
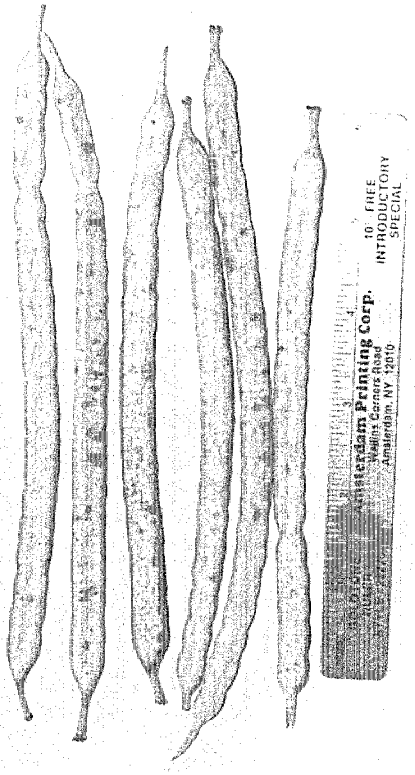
FIG. 4 is a color photograph of the pods of the tree.
Figure 5:
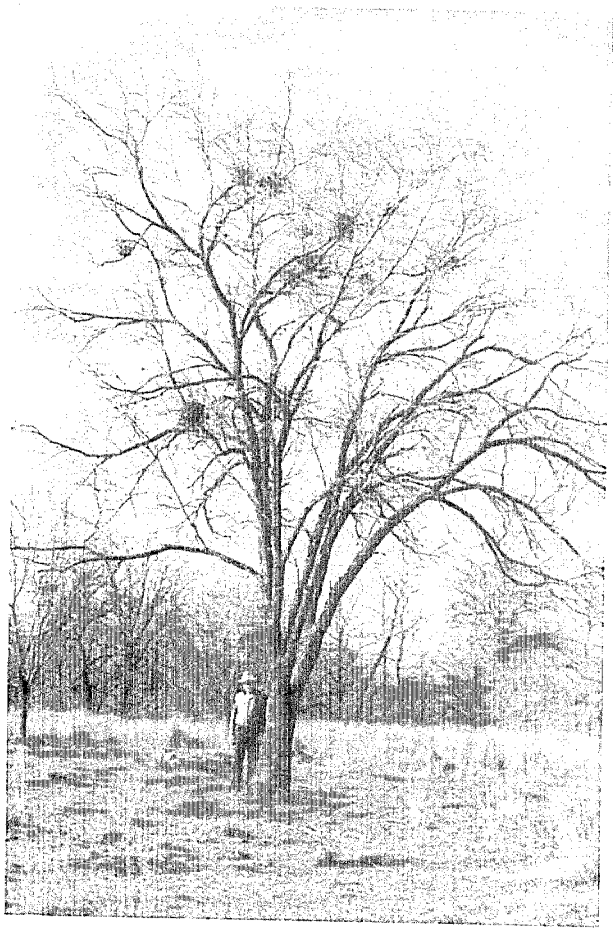

The following is a detailed description of our new variety of *Prosopis glandulosa* var. glandulosa.

Tree: Open, single-stemmed at the base with inverted conical form. The approximately 30 year old parent specimen had a height of 10.5 m and a diameter at breast height of 42 cm.

Branch angle: Major branches have an subtend an angle of 20–25 degrees with the main truck. The bark color of the main trunk is Black Group 202 B.

Foliage: There is one pair of pinnae per leaf. Individual pinnae 120–130 mm long. About 10 pair of leaflets per pinnae spaced about 6 mm apart. Leaflets are 4–5 mm wide and 20–25 mm long. The internode distance along the stem ranges from 4–5 cm. In contrast to the 25–30 degree angle between internode segments on standard thorny native mesquites, the angle between internode segments on this invention is always less than 10 degrees and often indistinguishable from zero degrees. The color of the younger leaves, according to the Royal Horticultural Society Color chart are Green group 143 A while the older leaves vary between Green Group 137 B and C.

Thorns: The tree is virtually thornless, but at some times of the year, small (1 mm diameter and 6 mm long) semi-herbaceous thorns may appear. This is in contrast to woody, 2–4 cm diameter long, 3 mm basal diameter thorns characteristic of the species.

Hardiness: When properly hardened off in mid-winter, the tree will withstand 3 consecutive days below freezing with absolute minimums of −15 C. on each of the days without any damage. The maximum temperature sustained by the tree was 41 C. In many summers it is not unusual for the tree to be without rain for 60–90 days when daily maximum temperatures are 35 C. or greater. Under these conditions the tree exhibits no apparent damage. No irrigation is required for this tree in major Texas cities.

Cotton root rot resistance: Complete resistance to this root rot pathogen.

Parentage: A chance seedling of unknown parentage.

Propagation: Holds to distinguishing characteristics through succeeding propagation by grafting, air layering or mist propagation of unrooted cuttings.

Localities where grown and observed: Seguin, Tex. and Kingsville, Tex.

Flowering habits: In Stockdale, Tex. the tree begins to flower in March and may flower until September. However the peak flowering period is in April and May. The perfect flowers are reported to be self-incompatible. The peak pod ripening stage is begins in mid June. The mature pods range are about 0.9 cm in width, 0.5 cm in thickness and are 17 to 20 cm in length. The basal color of the pods (according to Royal Society of Horticulture Color Charts) is yellow orange group 16D. The purple mottling in the pods ranges from red purple group 59 A to 59 C. Fully developed pods contain 21 +/−1.7 seeds that have a 50 seed weight of 2.337 g (46.7 mg/seed). The pods are sweet to the taste with a mild aftertaste. The seeds are about 4.8 mm wide vary in length from 6–7 mm. The seed color is greyed orange group 165B.

We claim:

1. A new and distinct variety of mesquite tree, *Prosopis glandulosa* var. glandulosa, substantially as illustrated and described, running true to the parent tree, which has a cold tolerance of −15 C., further characterized by being thornless, has much more of an erect habit, with smaller branch angles than the typical mesquite, does not have a typical weeping habit typical of native mesquites.

* * * * *